(12) United States Patent
Carmon et al.

(10) Patent No.: US 10,429,669 B2
(45) Date of Patent: Oct. 1, 2019

(54) METHOD AND SYSTEM FOR IMPROVING AN OPHTHALMIC PRESCRIPTION

(71) Applicant: SHAMIR OPTICAL INDUSTRY LTD., Upper Galilee (IL)

(72) Inventors: Yuval Carmon, Kiryat Tivon (IL); Liron Gleser, Rosh Pinna (IL); Yotam Gil, Kiryat Tivon (IL)

(73) Assignee: SHAMIR OPTICAL INDUSTRY LTD., Upper Galilee (IL)

( * ) Notice: Subject to any disclaimer, the term of this patent is extended or adjusted under 35 U.S.C. 154(b) by 0 days.

(21) Appl. No.: 14/381,883

(22) PCT Filed: Feb. 19, 2013

(86) PCT No.: PCT/IL2013/050144
§ 371 (c)(1),
(2) Date: Aug. 28, 2014

(87) PCT Pub. No.: WO2013/128439
PCT Pub. Date: Sep. 6, 2013

(65) Prior Publication Data
US 2015/0077704 A1    Mar. 19, 2015

Related U.S. Application Data

(60) Provisional application No. 61/605,368, filed on Mar. 1, 2012.

(51) Int. Cl.
*G02C 7/02* (2006.01)
*A61B 3/028* (2006.01)
*G06F 17/50* (2006.01)

(52) U.S. Cl.
CPC ............. *G02C 7/027* (2013.01); *A61B 3/028* (2013.01); *G06F 17/5009* (2013.01)

(58) Field of Classification Search
CPC .............................................. G02C 7/022–028
(Continued)

(56) References Cited

U.S. PATENT DOCUMENTS

| 6,655,803 | B1 | 12/2003 | Rubinstein et al. |
| 6,661,523 | B1 | 12/2003 | Rubinstein et al. |

(Continued)

FOREIGN PATENT DOCUMENTS

| EP | 1138253 | 10/2001 |
| EP | 2253990 | 11/2010 |

(Continued)

OTHER PUBLICATIONS

Stavroudis, "Simpler derivation of the formulas for generalized ray tracing", Journal Optical Society of America, vol. 66, No. 12, Dec. 1976, 1330-1333.

(Continued)

*Primary Examiner* — Darryl J Collins
*Assistant Examiner* — Journey F Sumlar
(74) *Attorney, Agent, or Firm* — Dorsey & Whitney LLP (57) ABSTRACT

A method for adjusting an original prescription to be used in manufacturing an ophthalmic lens for correcting vision of a patient, the method comprising: obtaining an original prescription based on an eye vision measurement performed by virtue of a real optical system; obtaining supplementary input data associated with the eye vision measurement; calculating a simulated optical system simulating the real optical system, by using at least the original prescription and the supplementary input data; and calculating an adjusted prescription by using at least the original prescription and the simulated optical system, to reflect the effect of the supplementary input data on the eye vision measurement.

8 Claims, 5 Drawing Sheets

(58) Field of Classification Search
USPC ........................................ 351/159.74–159.75
See application file for complete search history.

(56) References Cited

U.S. PATENT DOCUMENTS

| | | |
|---|---|---|
| 6,755,524 B2 | 6/2004 | Rubinstein et al. |
| 6,824,268 B2 | 11/2004 | Rubinstein et al. |
| 7,726,813 B2 | 6/2010 | Dai |
| 7,744,217 B2 | 6/2010 | Cabeza et al. |
| 7,931,371 B2 | 4/2011 | Dai |
| 7,931,374 B2 | 4/2011 | Dai et al. |
| 7,972,000 B2 | 7/2011 | Becker et al. |
| 2007/0195265 A1* | 8/2007 | Dreher .................. G02C 13/003 351/159.73 |
| 2008/0100800 A1 | 5/2008 | Guillen et al. |
| 2010/0039614 A1 | 2/2010 | Morris et al. |
| 2010/0114540 A1 | 5/2010 | Shinohara et al. |
| 2010/0182566 A1 | 7/2010 | Becker et al. |
| 2012/0016645 A1 | 1/2012 | Altheimer et al. |
| 2012/0033179 A1 | 2/2012 | Kratzer et al. |

FOREIGN PATENT DOCUMENTS

| | | |
|---|---|---|
| WO | WO 2004053568 | 6/2004 |
| WO | WO2010/132304 | 11/2010 |

OTHER PUBLICATIONS

Wilson, David, "Vertex distance and pantoscopic angle—a review", Jan. 1, 2015, XP055386450.

* cited by examiner

METHOD AND SYSTEM FOR IMPROVING AN OPHTHALMIC PRESCRIPTION

TECHNICAL FIELD

This invention relates to prescriptions for eyeglass ophthalmic lenses, and in particularly to methods for improving the values of these prescriptions.

BACKGROUND DESCRIPTION

People suffering from poor visual acuity many times find relief by using vision correcting lenses, i.e., ophthalmic lenses. These may come in the form of corrective lenses fitted into eyeglasses. For their manufacturing, the desired optical characteristics of the ophthalmic lenses (e.g., sphere power, cylinder and cylinder axis) are determined in the following way: the patient is given a visual acuity test (i.e., eye vision measurement procedure)—be it objective (using an auto-refractometer for example), or subjective (using a trial frame or a phoropter fitted with trial lenses). The outcome of the test is a prescription (i.e., original prescription) according to which the ophthalmic lenses for correcting the patient's vision can be manufactured.

When considering patients suffering from myopia or presbyopia, the patient goes through an eye vision measurement procedure for determining his prescription for far vision and/or near vision correction. In this procedure the patient is usually instructed to read a hand held book (in near vision measurement) or to look at a testing board with symbols (in far vision measurement) using different correctional lenses. The optimal correction lenses for far vision and/or near vision are then selected, and the far vision and/or near vision prescription is prescribed to the patient by the prescriber.

The existing different eye vision measurements are performed according to various procedural protocols and under different conditions. These procedures are characterized by a plurality of parameters which influence on each eye vision measurement, and usually are not taken into consideration when a prescription is provided to the patient. These parameters can be geometrical and optical parameters that can be expressed by means of distances, angles, and optical characterizing parameters. Instead of taking into consideration the different values of these parameters, usually default values are used. This lack of uniformity between the parameters, and the use of default values for these parameters, usually results in inaccuracy in the prescription that is provided to the patient.

SUMMARY OF THE PRESENTLY DISCLOSED SUBJECT MATTER

The presently disclosed subject matter discloses system and method for adjusting an original prescription (known in the art standard ophthalmic prescription) to be used in manufacturing eyeglass ophthalmic lenses for correcting vision of a patient. The presently disclosed system and method compensate the difference between the ophthalmic lenses as prescribed a prescriber (e.g., optometrist, ophthalmologist) and the lenses' optical performance as perceived by the patient. According to the presently disclosed subject matter, in order to perform this compensation, a set of supplementary input data can be added to the original prescription in order to improve the accuracy of matching the ophthalmic lenses to the patient. As a result of this compensation, an adjusted prescription, which is based on the original prescription and on the supplementary input data, is calculated.

The adjusted prescription can be used for manufacturing ophthalmic lenses, or it can be used for calculating an as-worn compensated prescription in which the chosen frame of the ophthalmic lenses is taken into consideration, and only then the ophthalmic lenses will be manufactures based on the compensated prescription.

The term 'FV' refers to a far vision eye vision measurement procedure, or a far distance in which it is performed, in which an original prescription is prescribed to a patient's ophthalmic lenses for correcting myopia or hyperopia.

The term 'NV' refers to a near vision eye vision measurement procedure, or a near distance in which it is performed, in which an original prescription is prescribed to a patient's ophthalmic lenses for correcting presbyopia.

The term 'BVD' refers to Back Vertex Distance which is the distance between the back of the lenses and the front of the patient's eyes.

The term 'original prescription' refers hereinafter to a well known in the art order written by an eyeglass prescriber (e.g., optometrist, ophthalmologist) that specifies the values of all parameters the prescriber has deemed necessary to construct and/or dispense ophthalmic lenses appropriate for a patient. The parameters which can be included in the original prescription for each eye of the patient are the following: FV sphere power, FV cylinder power, FV cylinder axis, FV prism power and direction, FV base, NV sphere power, NV addition power, NV cylinder power, NV cylinder axis, NV prism power and direction, NV base, and pupillary distance.

The term 'adjusted prescription' refers hereinafter to a set of parameters which are calculated by the system of the presently disclosed subject matter according to the original prescription combined with the supplementary input data, according to a method detailed below. The parameters that can be included in the adjusted prescription are the following: FV sphere power, FV cylinder power, FV cylinder axis, FV prism power and direction, FV base, NV sphere power, NV addition power, NV cylinder power, NV cylinder axis, NV prism power and direction, NV base, and pupillary distance. These are adjusted values of the corresponding parameters in the original prescription.

The term 'compensated prescription' or 'as-worn compensated prescription' refers hereinafter to a set of parameters which are calculated by the system of the presently disclosed subject matter according to said the adjusted prescription after taking into consideration the properties of the patient's chosen frame for the ophthalmic lenses. The parameters that can be included in the compensated prescription are the following: FV sphere power, FV cylinder power, FV cylinder axis, FV prism power and direction, FV base, NV sphere power, NV addition power, NV cylinder power, NV cylinder axis, NV prism power and direction, NV base, and pupillary distance. These are adjusted values of the corresponding parameters in the adjusted prescription.

In accordance with one aspect of the presently disclosed subject matter there is provided a method for adjusting an original prescription to be used in manufacturing an ophthalmic lens for correcting vision of a patient. The method comprises:
(a) obtaining an original prescription based on an eye vision measurement performed by virtue of a real optical system;
(b) obtaining supplementary input data associated with the eye vision measurement;

(c) calculating a simulated optical system simulating the real optical system, by using at least the original prescription and the supplementary input data; and (d) calculating an adjusted prescription by using at least the original prescription and the simulated optical system, to reflect the effect of the supplementary input data on the eye vision measurement.

The real optical system can include at least one of: real eye of the patient, a real measuring instrument and at least one of NV and FV real source objects used for the eye vision measurement.

The supplementary input data can comprise at least one of: eye data, measuring instrument data, and source object data.

The simulated optical system can comprise at least one of:
(i) at least one simulated eye of the patient simulating the real eye of the patient;
(ii) a simulated measuring instrument simulating the real measuring instrument;
(iii) a FV simulated source object simulating the FV real source object; and
(iv) a NV simulated source object simulating the NV real source object.

The step of calculating a simulated optical system, as defined above, can comprise:
(a) calculating the FV simulated source object or the NV simulated source object by using the source object data;
(b) calculating the simulated measuring instrument by using the measuring instrument data and the original prescription; and
(c) calculating the simulated eye of the patient by using the eye data.

The source object data can comprise at least one of: FV object distance from patient, FV usage of mirrors, FV height of FV object with respect to the floor, FV vertical height of patient's eye from the floor, FV vertical height difference between the FV object and the patient's eye, and FV compensation of lens sphere power measurement, NV object distance measurement, NV vertical observation angle of patient, phoropter lens diameter, and trial frame lens diameter.

The FV simulated source object can be configured to simulate position of the FV real source object in the real optical system by using at least one of: the FV object distance from patient, the FV usage of mirrors, the FV height of FV object with respect to the floor, the vertical height of patient's eye from the floor, FV vertical height difference between the FV object and the patient's eye, and the FV compensation of lens sphere power measurement.

The NV simulated source object can be configured to simulate position of the NV real source object in the real optical system by using at least one of: the NV object distance measurement, the NV vertical observation angle of patient, the phoropter lens diameter, and the trial frame lens diameter.

The measuring instrument data can comprise at least one of: FV BVD between the measuring instrument and the eye of the patient, FV taking into consideration of the BVD, NV BVD between the measuring instrument and the eye of the patient, NV taking into consideration of the BVD, FV type of measuring instrument, NV type of measuring instrument, phoropter parameters, trial frame parameters, FV number of lenses and their position in trial frame slots, NV number of lenses and their position in trial frame slots, FV vertical tilt of the measuring instrument, NV vertical tilt of the measuring instrument, FV horizontal tilt of the measuring instrument, NV horizontal tilt of the measuring instrument, FV vertical observation angle of patient, NV vertical observation angle of patient, FV horizontal observation angle of patient, NV horizontal observation angle of patient, and method of addition power test and purpose of each lens used in a trial frame.

The phoropter parameters can include at least one of the following: usage of phoropter in FV, usage of phoropter in NV, phoropter brand, phoropter model, phoropter lens geometry, phoropter lens refraction index, phoropter lens center thickness, phoropter lens edge thickness, and phoropter lens diameter; and wherein the trial frame parameters include at least one of the following: usage of trial frame in FV, usage of trial frame in NV, trial frame brand, trial frame model, trial frame lens geometry, trial frame lens refraction index, trial frame lens center thickness, trial frame lens edge thickness, and trial frame lens diameter.

The simulated measuring instrument can be configured to:
(i) simulate position of the real measuring instrument in the real measurement system by using at least one of: the FV BVD between the measuring instrument and the eye of the patient, the FV taking into consideration of the BVD, the NV BVD between the measuring instrument and the eye of the patient, the NV taking into consideration of the BVD, the FV type of measuring instrument, the NV type of measuring instrument, the phoropter parameters, the FV number of lenses and their position in trial frame slots, and the NV number of lenses and their position in trial frame slots;
(ii) simulate orientation of the real measuring instrument in the real measurement system by using at least one of: the FV vertical tilt of the measuring instrument, the NV vertical tilt of the measuring instrument, the FV horizontal tilt of the measuring instrument, the NV horizontal tilt of the measuring instrument, the FV vertical observation angle of patient, the NV vertical observation angle of patient, the FV horizontal observation angle of patient, the NV horizontal observation angle of patient; and
(iii) simulate optical and geometrical characteristics of the real measuring instrument in the real measurement system by using at least one of: the phoropter parameters, the trial frame parameters.

The eye data can comprise at least one of: FV strength of illumination during the eye vision measurement, NV strength of illumination during the eye vision measurement, FV pupil diameter, NV pupil diameter, FV horizontal tilt of the measuring instrument, NV horizontal tilt of the measuring instrument, NV object distance measurement, FV horizontal observation angle of patient, and NV horizontal observation angle of patient.

The simulated eye of the patient is configured to:
(iv) simulate dimensions of the real eye's pupil by using at least one of: the FV strength of illumination during the eye vision measurement, the NV strength of illumination during the eye vision measurement, the FV pupil diameter, and the NV pupil diameter;
(v) simulate position and orientation of the real eye by using at least one of: the FV horizontal tilt of the measuring instrument, the NV horizontal tilt of the measuring instrument, the NV object distance measurement, the FV horizontal observation angle of patient, and the NV horizontal observation angle of patient; and
(vi) simulate distance of reference refraction surface of the real eye by using at least one of: FV BVD between the measuring instrument and the eye of the patient, and NV BVD between the measuring instrument and the eye of the patient.

The step of calculating an adjusted prescription, as defined above, can be performed by simulating tracing of wave fronts from the FV or NV simulated source object through the simulated measurement instrument towards the simulated eye.

The supplementary input data can comprise a measurement data which is updated in each eye vision measurement, and a general data which is patient-independent and is related to the environment of the eye vision measurement and the real optical system.

The method of the presently disclosed subject matter can further comprise steps of: obtaining frame parameters associated with a frame of the ophthalmic lens; and calculating an as-worn compensated prescription based on the adjusted prescription and the frame parameters.

The method of the presently disclosed subject matter can further comprise a step of calculating a fitted optical system simulating a patient-frame optical system, by using at least the frame parameters.

The frame parameters can include at least one of the following: frame pantoscopic tilt, frame panoramic tilt, frame BVD, frame width, frame height, bridge width, and distance between lenses.

The method of the presently disclosed subject matter can further comprise a step of: providing the as-worn compensated prescription to an ophthalmic lens manufacturing machine, thereby manufacturing the ophthalmic lens.

In accordance with another aspect of the presently disclosed subject matter there is provided a method for manufacturing an ophthalmic lens, comprising:
(a) obtaining an original prescription based on an eye vision measurement performed by virtue of a real optical system;
(b) obtaining supplementary input data associated with the eye vision measurement;
(c) calculating a simulated optical system simulating the real optical system, by using at least the original prescription and the supplementary input data;
(d) calculating an adjusted prescription by using at least the original prescription and the simulated optical system, to reflect the effect of the supplementary input data on the eye vision measurement;
(e) obtaining frame parameters associated with a frame of the ophthalmic lens;
(f) calculating a fitted optical system simulating a patient-frame optical system, by using at least the frame parameters;
(g) calculating an as-worn compensated prescription based on the adjusted prescription and the frame parameters;
(h) providing the as-worn compensated prescription to an ophthalmic lens manufacturing machine.

The supplementary input data can include data as defined above. The simulated optical system and the real optical system can be defined as mentioned above.

In accordance with another aspect of the presently disclosed subject matter there is provided a method for prescribing an original prescription based on an eye vision measurement performed by virtue of a real optical system for an ophthalmic lens for correcting vision of a patient. The method comprises a step of providing supplementary input data associated with an eye examination in which the original prescription was obtained, wherein the supplementary input data comprises at least one of: eye data, measuring instrument data, and source object data.

The supplementary input data can include data as defined above.

In accordance with another aspect of the presently disclosed subject matter there is provided a prescription for an eye of a patient that comprises an original prescription for an ophthalmic lens for correcting vision of a patient, and supplementary input data associated with an eye examination in which the original prescription was obtained, wherein the supplementary input data comprises at least one of: eye data, measuring instrument data, and source object data.

The supplementary input data can be used for adjusting an original prescription to be used in manufacturing an ophthalmic lens for correcting vision of a patient according to the method of manufacturing that is defined above.

The supplementary input data defined above can be carried by a data carrying medium.

The method of the presently disclosed subject matter, according to its different aspects, can be performed by an electronic processing system having an electronic processor and a computer readable medium. The computer readable medium can be configured to store instructions that, when executed by the electronic processor, cause the electronic processor to perform the steps of the method.

BRIEF DESCRIPTION OF THE DRAWINGS

In order to understand the invention and to see how it can be carried out in practice, embodiments will now be described, by way of non-limiting examples only, with reference to the accompanying drawings, in which.

DETAILED DESCRIPTION OF EMBODIMENTS

Figure 1A:
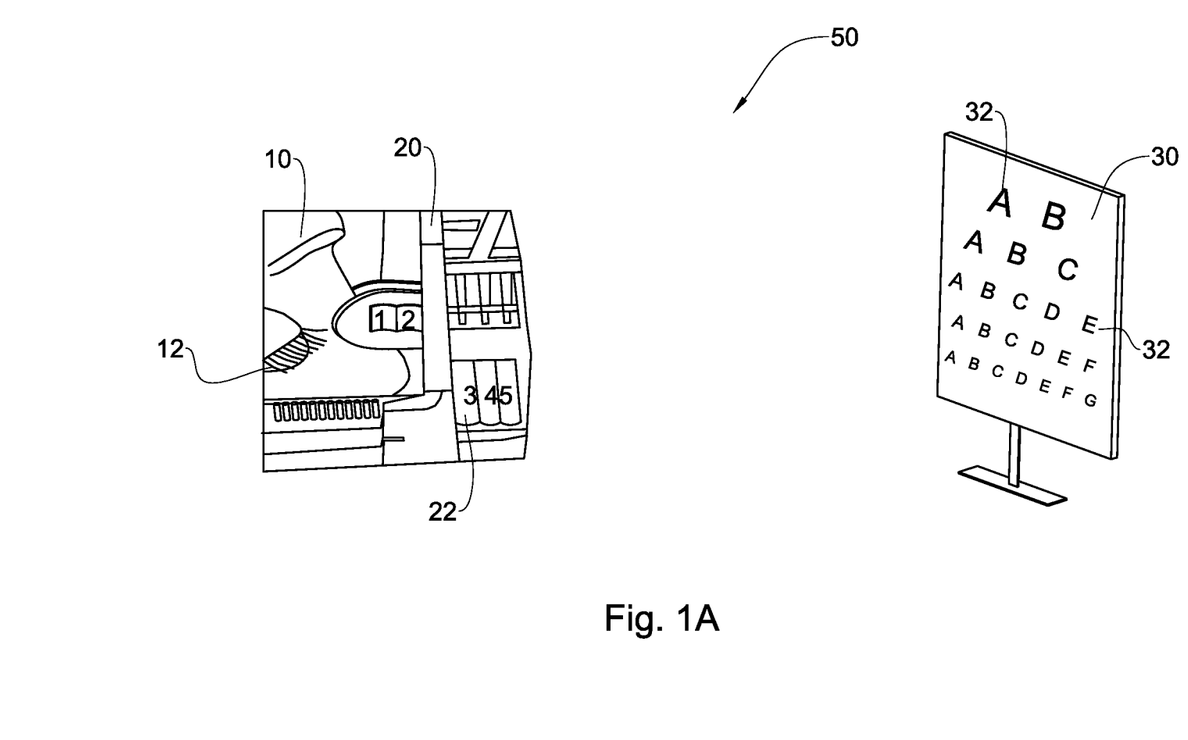
FIG. 1A schematically illustrates an example of a known in the art FV eye vision measurement system, from which a FV original prescription can be obtained.

Reference is now made to FIG. 1A which schematically illustrates an example of a known in the art FV eye vision measurement system 50. According to this example, a FV eye vision measurement is performed when the patient 10 views a FV source object, i.e., a testing board 30, and recognized the symbols 32 of this board according to a specific known measurement protocol. In order to view the symbols 32, the patient 10 uses his eyes 12 which are directed towards the testing board 30 through a measurement instrument, i.e., a trial frame 20. During this eye vision measurement, the prescriber replaces the correction lenses of the trial frame within frames 22 so as to find the optimal correction lenses with which the person can recognize the symbols 32 correctly. Following the FV eye vision measurement, an original prescription is prescribed to the patient for specific ophthalmic correction lenses.

Figure 1B:
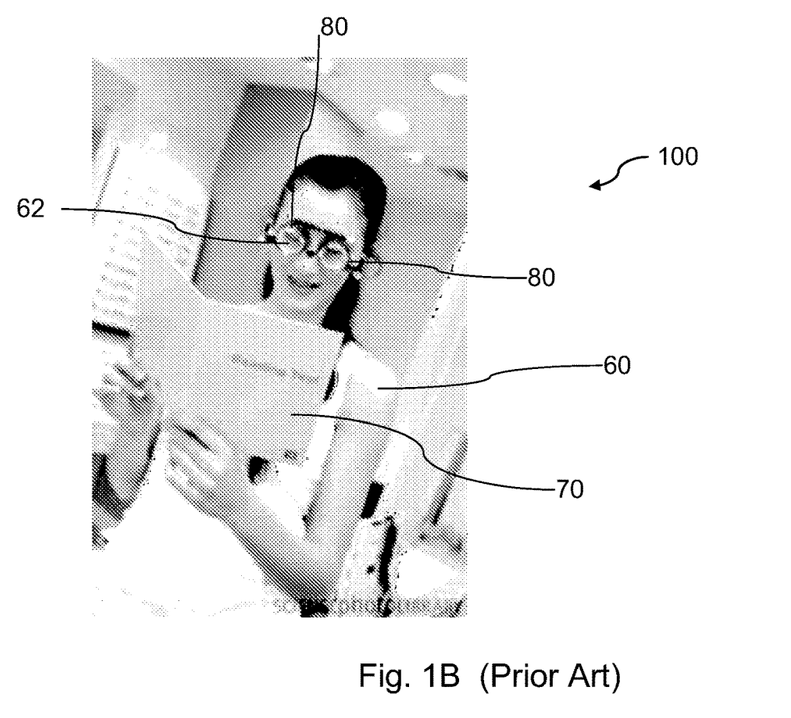
FIG. 1B schematically illustrates an example of a known in the art NV eye vision measurement system, from which a NV original prescription can be obtained.

FIG. 1B schematically illustrates an example of a known in the art NV eye vision measurement system 100. According to this example, a NV eye vision measurement is performed when the patient 60 views a NV source object, i.e., a book 70, and recognized the text of this book according to a specific known in the art protocol. In order to view the text of the book 70, the patient 60 uses his eyes 62 which are directed towards the book 70 through a measurement instrument, i.e., a trial frame 80. During this measurement, the prescriber replaces the correction lenses of the trial frame 80 so as to find the optimal correction lenses with which the person can read the text of the book 70 without any difficulties. Following this NV eye vision measurement, an original prescription is prescribed to the patient for specific ophthalmic correction lenses.

Figure 1C:
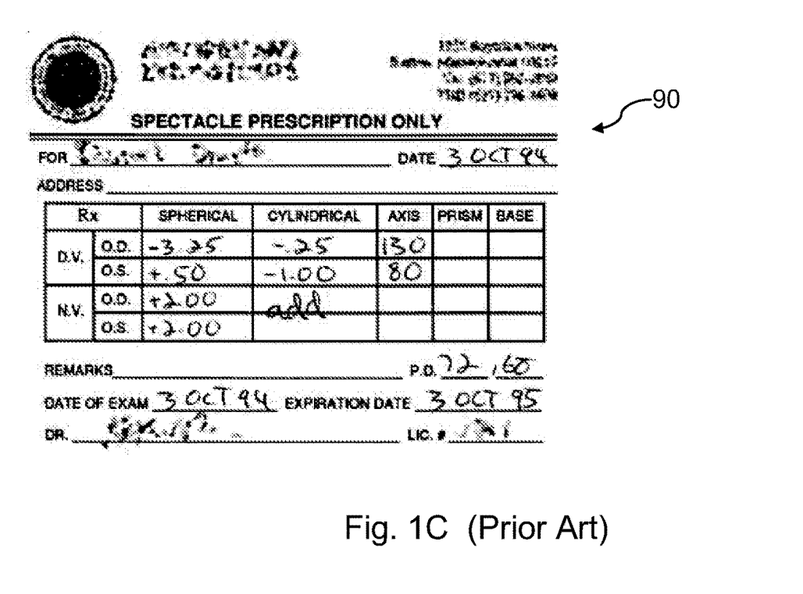
FIG. 1C schematically illustrates an example of a known in the art original prescription which can be provided to a patient by a prescriber following FV and NV eye vision measurement procedures.
Figure 3:
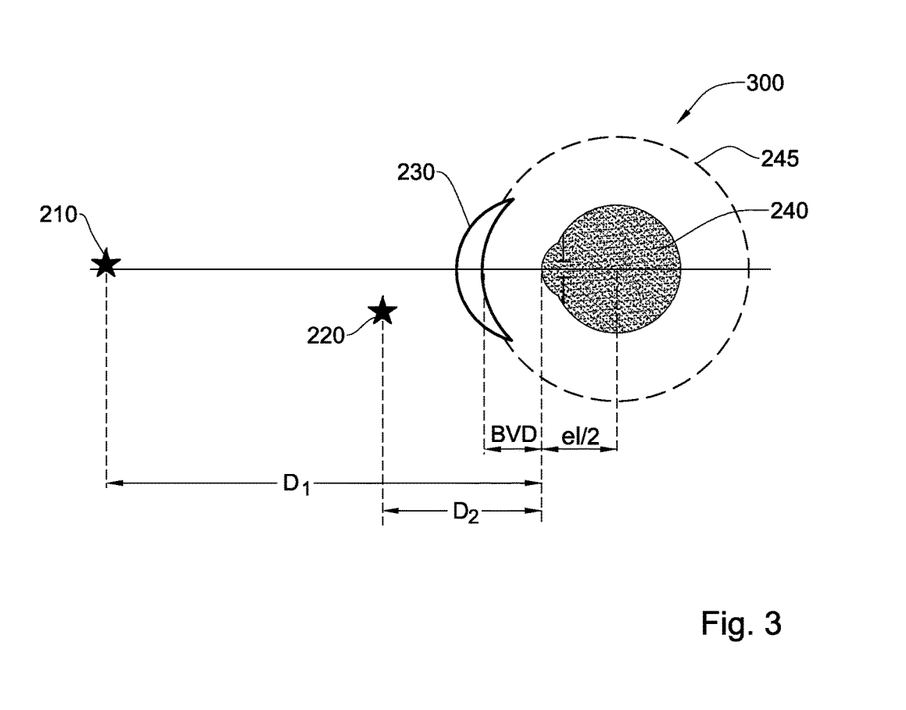
FIG. 3 schematically illustrates a simulated optical system as being calculated by the system of the presently disclosed subject matter.

FIG. 1C illustrates an example of a known in the art original prescription 90 which can be provided to a patient by a prescriber (e.g., optometrist, ophthalmologist) following the eye vision measurement procedures of FIGS. 1A and 1B. As can be seen from FIG. 1C, the values of the original prescription are represented in a table. The original prescription of FIG. 3 is provided after FV and NV eye vision measurement procedures.

The known in the art vision measurement procedures that are exemplary disclosed in FIGS. 1A and 1B are characterized and/or depend on a variety of parameters which can influence of the selection of the optimal correction lenses for the patient, and as a result of that on the original prescription 90 according to which the ophthalmic lenses will be manufactured. These parameters that influence on the final original prescription that is prescribed to the patient are referred hereinafter as 'supplementary input data'. The supplementary input data can be represented by a set of values that depend on different factors such as: the environment of the eye vision measurement, the characteristics of the measurement instrument, the measurement method and the patient's personal parameters. These factors are usually not taken into consideration when the original prescription 90 is prescribed. In order take these factors into consideration, and thereby improve the accuracy of the original prescription 90, the presently disclosed subject matter uses the method of FIGS. 2A and 2B as will be detailed below. This method uses the supplementary input data that is related to eye vision measurement procedure in order to improve the accuracy of the known in the art original prescription 90. By this adjustment, the influence of the supplementary input data on the lenses' optical performance as perceived by the patient is taken into consideration, and this provides a much accurate adjusted prescription according to which the ophthalmic lenses can be manufactured.

Figure 2A:
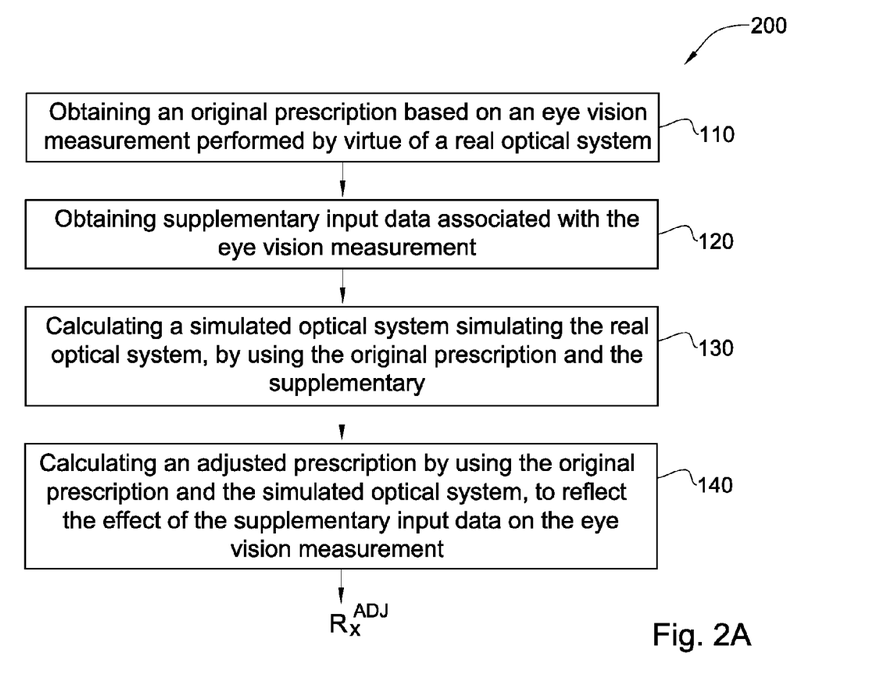
FIG. 2A generally illustrates the steps of the method according to the presently disclosed subject matter, which can be performed by the system of the presently disclosed subject matter for adjusting the original prescription, and calculating an adjusted prescription.

Reference is now made to FIG. 2A which generally illustrates the steps of a method 200 which can be performed by the system of the presently disclosed subject matter for adjusting the original prescription 90 to be used in the manufacturing of ophthalmic lenses for spectacles that will be used for correcting vision of a patient.

In Step 110 of the method 200, the original prescription 90 is obtained based on an eye vision measurement performed by virtue of a real optical system. The real optical system is defined as the whole system in which the eye vision measurement was performed. This system includes the following components: the real eyes of the patient, the real measuring instrument and at least one of NV and FV real source objects used for the eye vision measurement. For example, FIG. 1A illustrates a real optical system for FV eye vision measurement that is defined by the eyes 12, the trial frame 20 (the real measuring system), and the testing board 30 (the FV real source object). For another example, FIG. 1B illustrates a real optical system for NV eye vision measurement that is defined by the eyes 62, the trial frame 80 (the real measuring system) and the book 70 (the NV real source object).

Figure 5:
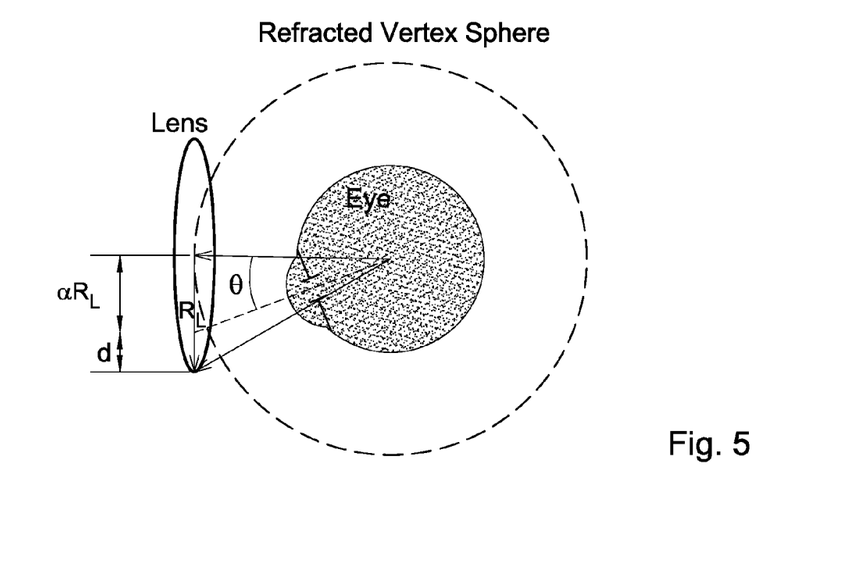
FIG. 5 schematically illustrates the angle of gaze θ for NV, calculated from the test lens diameter (either phoropter or trail frame).

In step 120 of the method 200, the supplementary input data is obtained. The supplementary input data is associated with the eye vision measurement procedure and can be divided to the following three main groups: 1. source object data; 2. measuring instrument data; and 3. eye data. Each group has a plurality of parameters, the value of which can be provided by the prescriber, any party involved in the process of prescribing and/or manufacturing the lenses. Alternatively or additionally, these parameters can receive default values which are known in the art. The presently disclosed method 200 can use at least some or all the value of these parameters. The content of the parameters of each group is detailed below as follows:

1. The source object data:
   a. FV object distance from patient—this parameter estimates the distance between the patient's eyes and the FV real source object (e.g., printed board, projector's screen, computer screen). This parameter is calculated according to the function: $D_{scr}=\sqrt{D_{wall}^2+(H_{scr}-H_{eye})^2}$, where $D_{scr}$ is the FV object distance from patient, $D_{wall}$ is the horizontal distance between the patient's eyes and the FV source object, $H_{scr}$ is item 1.c. below, $H_{eye}$ is item 1.d. below. The distance $D_{scr}$ helps correcting the needed sphere power, $S_c=S_m-1/D_{scr}$, where $S_c$ is the compensated sphere power, and $S_m$ is the measured sphere power in the original prescription. The value of the FV object distance from patient can be between 2 and 8 meter; its default value is 6 meter; and it can be measured by a ruler or a tape measure.
   b. FV usage of mirrors—this parameter receives the value of Yes/No; If the value is Yes, than the parameter $D_{wall}$ of item 1.a. is calculated according to the effective optical distance; and if the value is No, than $D_{wall}$ is not changed.
   c. FV height of FV object with respect to the floor—this parameter estimates the height in which the FV source object is located with respect to the floor; its value can be of up to 3 meter; its default value is the same as in item 1.d., and it can be measured by a ruler or a tape measure.
   d. FV vertical height of patient's eye from the floor—this parameter estimates the vertical distance between the patient's eyes and the floor; its value can be between 80 and 180 cm; its default value can be 130 cm; and it can be measured by a ruler or a tape measure. By using the values of FV height of FV object with respect to the floor and FV vertical height of patient's eye from the floor, or by any other calculation, and additional parameter of FV vertical height difference between the FV object and the patient's eye can be provided.
   e. FV compensation of lens sphere power measurement—this parameter receives the value of Yes/No, according to the answer of the question: "Is the lens sphere power measurement is compensated according to the additional accommodation which emerges due to the difference between the refraction to infinity and the refraction to the actual distance?".

f. NV object distance measurement—this parameter helps placing the NV object in its correct position in the simulation and to estimate the NV pupillary distance; its value can be between 20 and 60 cm, usually between 35 and 45 cm; its default value can be 40 cm; and it can be measured by one of: a ruler, a tape measure, camera(s)+computer vision system, a visual estimation.

g. NV vertical observation angle of patient—this parameter defines the observation angle (up/straight/down) of the patient in the NV vision measurement; its value can be between 75° down and 10° up; its default value is 0°; and it can be measured by one of: a ruler, a tape measure, camera(s)+computer vision system, a visual estimation.

h. phoropter lens diameter—this parameter affects the location on the lens through which the user views the NV source object, and therefore the amount of the oblique refraction present in the vision measurement. A larger diameter allows the patient to look through a lower part of the lens and therefore affect the parameters that influence on the oblique refraction; this parameters is used for calculating θ, the angle of gaze, which is schematically shown in FIG. 5; e.g. $\theta=\tan^{-1}(\alpha R_L/R_{VD})$, when $R_L$ is the phoropter lens radius (half of the phoropter lens diameter), $R_{VD}$ is the refracted vertex distance, and α is a scale factor (α value can be between 0.5 and 1; its default value can be 0.75). Or $\theta=\tan^{-1}[(R_L-d)/R_{VD}]$, when d is the offset distance from the lens bottom edge (d can be between 0 to $R_L$; its default value can be 2 mm); the value of the phoropter lens diameter can be taken from the specification of the phoropter that was used during the vision measurement or from parameter 2.g. below, or it can be measured by a caliper or a ruler; its value can be up to 25 mm; its default value is 25 mm.

i. trial frame lens diameter—this parameter affects the location on the lens through which the user views the NV source object, and therefore the amount of the oblique refraction present in the vision measurement. A larger diameter allows the patient to look through a lower part of the lens and therefore affect the parameters that influence on the oblique refraction; this parameters is used for calculating θ, the angle of gaze, which is schematically shown in FIG. 5; e.g. $\theta=\tan^{-1}(\alpha R_L/R_{VD})$, when $R_L$ is the trial frame lens radius (half of the trial frame lens diameter), $R_{VD}$ is the refracted vertex distance, and α is a scale factor (α value can be between 0.5 and 1; its default value can be 0.75). Or $\theta=\tan^{-1}[(R_L-d)/R_{VD}]$, when d is the offset distance from the lens bottom edge (d can be between 0 to $R_L$; its default value can be 2 mm); the value of the trial frame lens diameter can be taken from the specification of the trial frame that was used during the vision measurement or from parameter 2.h. below, or it can be measured by a caliper or a ruler; its value can be up to 40 mm; its default value is 25 mm.

2. The measuring instrument data:

a. FV BVD between the measuring instrument in FV vision measurement and the eye of the patient—this parameter receives the value of the distance between the corneal apex of the patient's eyes and the measurement instrument, and is used in order to determine the position of the measurement instrument's lens and the patient's eyes; its value can be up to 40 mm; its default value can be the same as the chose frame BVD or 13 mm; its value can be measured by a ruler or a distometer.

b. FV taking into consideration of the BVD—this parameter receives the value of Yes/No according to the answer of the question: "Was the difference between the BVD of the measurement instrument and the chosen frame taken into consideration?"; if the value is Yes, then the parameter 2.a. is not used, and the value of the BVD of the chosen frame will be set to the value of the parameter 2.a.

c. NV BVD between the measuring instrument in NV vision measurement and the eye of the patient—this parameter receives the value of the distance between the corneal apex of the patient's eyes and the measurement instrument, and is used in order to determine the position of the measurement instrument's lens and the patient's eyes; its value can be up to 40 mm; its default value can be the same as the chose frame BVD or 13 mm; its value can be measured by a ruler or a distometer.

d. NV taking into consideration of the BVD—this parameter receives the value of Yes/No according to the answer of the question: "Was the difference between the BVD of the measurement instrument and the chosen frame taken into consideration?"; if the value is Yes, then the parameter 2.c is not used, and the value of the BVD of the chosen frame will be set to the value of the parameter 2.c.

e. FV type of measuring instrument—this parameter receives the value phoropter or trial frame. The value of this parameter can be for selecting the usage of the data of 2.g. or 2.h.

f. NV type of measuring instrument—this parameter receives the value phoropter or trial frame. The value of this parameter can be for selecting the usage of the data of 2.g. or 2.h.

g. phoropter parameters—this data set includes a plurality of parameters some of which can be taken from the specification of the phoropter; the phoropter parameters can include at least one of the following: usage of phoropter in FV (corresponding to 2.e.), usage of phoropter in NV (corresponding to 2.f.), phoropter brand, phoropter model, phoropter lens geometry (convex and concave lenses), phoropter lens refraction index, phoropter lens center thickness (for concave lenses), phoropter lens edge thickness (for convex lenses), and phoropter lens diameter (can be used for 1.h., or can receive the value of 1.h.).

h. trial frame parameters—this data set includes a plurality of parameters some of which can be taken from the specification of the trial frame; the trial frame parameters can include at least one of the following: usage of trial frame in FV (corresponding to 2.e.), usage of trial frame in NV (corresponding to 2.f.), trial frame brand, trial frame model, trial frame lens geometry (biconvex and biconcave lenses), trial frame lens refraction index, trial frame lens center thickness (for concave lenses), trial frame lens edge thickness (for convex lenses), and trial frame lens diameter (can be used for 1.ih., or can receive the value of 1.i.).

i. FV number of lenses and their position in trial frame slots—this parameter receives the number and the position of the lenses which were used during the FV vision measurement procedure when a trial frame was used; this parameter is divided to three sub-parameters, each of which can receive a value between 1 and 5, or NA, as follows: Sphere power: 1/2/3/4/5/NA; Cylinder power: 1/2/3/4/5/NA; Prism: 1/2/3/4/5/NA. The number of lenses which were used in the trial frame and its value can be between 1 and 5.

j. NV number of lenses and their position in trial frame slots—this parameter receives the number and the position of the lenses which were used during the NV vision measurement procedure when a trial frame was used; this parameter is divided to four sub-parameters, each of which can receive a value between 1 and 5, or NA, as follows: Sphere power: 1/2/3/4/5/NA; Cylinder power: 1/2/3/4/5/NA; Addition power: 1/2/3/4/5/NA; Prism: 1/2/3/4/5/NA. The number of lenses which were used in the trial frame, and its value can be between 1 and 5.

k. FV vertical tilt of the measuring instrument—this parameter receives the value of the vertical angle (pantoscopic/orthoscopic/retroscopic angle) of the measurement instrument in FV measurement; this parameter affects the amount of oblique refraction present in the vision measurement; its value can be up to 30°; its default value can be 0°; its value can be measured by an angle ruler (e.g., Shamir Panorameter™), cameras+computer vision system (e.g., Shamir Smart Centration System), or visual estimation.

l. NV vertical tilt of the measuring instrument—this parameter receives the value of the vertical angle (pantoscopic/orthoscopic/retroscopic angle) of the measurement instrument in NV measurement; this parameter affects the amount of oblique refraction present in the vision measurement; its value can be up to 30°; its default value can be 0°; its value can be measured by an angle ruler (e.g., Shamir Panorameter™), cameras+computer vision system (e.g., Shamir Smart Centration System), or visual estimation.

m. FV horizontal tilt of the measuring instrument—this parameter receives the value of the horizontal angle of the phoropter (if used) in FV measurement; this parameter affects the FV pupillary distance and the amount of oblique refraction in the vision measurement; its value can be up to 30°; its default value can be 0°; its value can be measured by an angle ruler (e.g., Shamir Panorameter™), cameras+computer vision system (e.g., Shamir Smart Centration System), or visual estimation.

n. NV horizontal tilt of the measuring instrument—this parameter receives the value of the horizontal angle of the phoropter (if used) in NV measurement; this parameter affects the NV pupillary distance and the amount of oblique refraction in the vision measurement; its value can be up to 30°; its default value can be 0°; its value can be measured by an angle ruler (e.g., Shamir Panorameter™), cameras+computer vision system (e.g., Shamir Smart Centration System), or visual estimation.

o. FV vertical observation angle of patient—this parameter receives the vertical angle (up/straight/down) in which the FV measurement was performed; this parameter affects the amount of oblique refraction in the vision measurement; its value can be between +20° (up) and −20° (down); its default value can be 0°; its value can be measured by a ruler and/or a tape measure, cameras+computer vision system, or visual estimation.

p. NV vertical observation angle of patient—this parameter receives the vertical angle (up/straight/down) in which the NV measurement was performed; this parameter affects the amount of oblique refraction in the vision measurement; its value can be between +10° (up) and −75° (down); its default value can be 0°; its value can be measured by a light meter, or by visual estimation, cameras+computer vision system, or visual estimation.

q. FV horizontal observation angle of patient—this parameter receives the horizontal angle (left/straight/right) in which the FV measurement was performed; this parameter affects the amount of oblique refraction in the vision measurement; its value can be between +45° and −45°; its default value can be 0°; its value can be measured by a light meter, or by visual estimation, cameras+computer vision system, or visual estimation.

r. NV horizontal observation angle of patient—this parameter receives the horizontal angle (left/straight/right) in which the NV measurement was performed; this parameter affects the amount of oblique refraction in the vision measurement; its value can be between +45° and −45°; its default value can be 0°; its value can be measured by a ruler and/or a tape measure, cameras+computer vision system, or visual estimation.

s. method of addition power test and purpose of each lens used in a trial frame—this parameter is used when a trial frame was used during the vision measurement procedure, and receives one of the values: "adding a separate addition lens"/"calculating the overall power including the FV sphere power".

3. The eye data:
a. FV strength of illumination during the eye vision measurement—this parameter receives one of the values: "full illumination"/"partial illumination"/"completely dark", according to the condition in which the FV measurement was performed; this parameter can determine the total luminous flux incident on the pupil; its value can be measured by a light meter, or by visual estimation; its default value is "full illumination".

b. NV strength of illumination during the eye vision measurement—this parameter receives one of the values: "full illumination"/"partial illumination"/"completely dark", according to the condition in which the FV measurement was performed; this parameter can determine the total luminous flux incident on the pupil; its value can be measured by a light meter, or by visual estimation; its default value is "full illumination".

c. FV pupil diameter—this parameter receives the diameter of the right and the left pupil in case of FV measurement; its default value is 4 mm; this parameter can be measured by an eye chart with pupil gauge, or by visual estimation.

d. NV pupil diameter—this parameter receives the diameter of the right and the left pupil in case of NV measurement; its default value is 4 mm; this parameter can be measured by an eye chart with pupil gauge, or by visual estimation.

The following parameters, which are defined above, can be also included in the eye data: FV horizontal tilt of the measuring instrument, NV horizontal tilt of the measuring instrument, NV object distance measurement, FV horizontal observation angle of patient, NV horizontal observation angle of patient, FV BVD between the measuring instrument in NV vision measurement and the eye of the patient.

The supplementary input data above can comprise a measurement data which is updated in each eye vision measurement, and a general data which is patient-independent and is related to the environment of the eye vision measurement and the real optical system. In other words, there are patient-independent parameters in supplementary input data that can be changed periodically (e.g., once a year), and there are parameters which are measurement-dependent, and are updated in each eye vision measurement procedure.

In one example, in addition to the original prescription that is usually provided, the optometrist will have to provide answers to the following exemplary questions as part of the supplementary input data in a special prescription (that includes the parameters of the original prescription and the parameters of the supplementary input data):

1. Far vision refraction:
   a. Illumination: full/partial/completely dark
   b. The patient vertical observation angle: up/straight/down.
      Angle estimation _________ degrees
   c. Vertical eye height from the floor cm
   d. The patient horizontal observation angle: left/straight/right.
      Angle estimation _________ degrees
   e. Pupil diameter as measured by the optometrist:
      Right pupil _________ mm
      Left pupil _________ mm
   f. Do you compensate the lens sphere power measurement according to the additional accommodation which emerges due to the difference between refraction to infinity and the refraction to the actual distance? Yes/No
   g. BVD _________ mm
   h. Do you take into consideration the differences between the BVD of the measuring instrument and the BVD of the chosen frame? Yes/No
2. Measuring instrument parameters for far vision refraction:
   a. Measuring instrument: phoropter/trial frame
   b. Vertical tilt: pantoscopic angle/orthoscopic angle/retroscopic angle.
      Angle estimation _________ degrees
   c. Horizontal tilt angle estimation _________ degrees (for phoropter)
   d. In case of using trial frame:
      A. Lens position in the slots of the trial frame:
         (i) Sphere power: 1/2/3/4/5/NA
         (ii) Cylinder power: 1/2/3/4/5/NA
         (iii) Prism: 1/2/3/4/5/NA
3. Near vision refraction:
   a. Illumination: full/partial/completely dark
   b. The patient vertical observation angle: up/straight/down.
      Angle estimation _________ degrees
   c. The patient horizontal observation angle: left/straight/right.
      Angle estimation _________ degrees
   d. Near distance measurement: _________._________ meters
   e. Pupil diameter as measured by the optometrist:
      Right pupil _________ mm
      Left pupil _________ mm
   f. BVD _________ mm
   g. Do you take into consideration the differences between the BVD of the measuring instrument and the BVD of the chosen frame? Yes/No
4. Measuring instrument parameters for near vision refraction:
   a. Measuring instrument: phoropter/trial frame
   b. Vertical tilt: pantoscopic angle/orthoscopic angle/retroscopic angle.
      Angle estimation _________ degrees
   c. Horizontal tilt angle estimation _________ degrees (currently relevant only for phoropter)
   d. In case of using trial frame:
      A. Method for addition power test: adding a separate addition lens/calculation of the overall power including the far vision sphere power (e.g. if the patient needs a far vision sphere correction of −1 [D] and an additional sphere power for near vision of +2, an optometrist that uses a trial frame can choose to use two lenses of −1 and +2 [D] and to put them in two different slots or to use a single lens of +1 [D] in a single slot)
      B. Lens position in the slots of the trial frame:
         (i) Sphere power: 1/2/3/4/5/NA
         (ii) Cylinder power: 1/2/3/4/5/NA
         (iii) Addition power: 1/2/3/4/5/NA
         (iv) Prism: 1/2/3/4/5/NA In another example, answers to the following question may be patient-independent, and may not be presented to the optometrist in every eye vision measurement procedure:

1. Far vision refraction:
   a. Measuring instrument: phoropter/trial frame
   b. Illumination: full/partial/completely dark
   c. Do you compensate the lens sphere power measurement according to the additional accommodation which emerges due to the difference between refraction to infinity and the refraction to the actual distance? Yes/No
2. Near vision refraction:
   a. Measuring instrument: phoropter/trial frame
   b. Illumination: full/partial/completely dark The rest of the parameters that might differ from one patient to another (patient-dependent) will be presented to the optometrist in each eye vision measurement procedure.

The answer to all the questions above, are inserted into the system of the presently disclosed subject matter and are being attributed to their corresponding parameters in the supplementary input data. For example, an answer to the question: "BVD: _________" in case of a FV procedure, will be attributed to the parameter: FV BVD between the measuring instrument in FV vision measurement and the eye of the patient.

Following the step 120, a step 130 of the method 200 is performed so as to calculate a simulated optical system that simulates the real optical system in which the eye vision measurement procedure has been performed. This calculation is performed by an Optical System Builder (OSB) algorithm that uses the original prescription and the supplementary input data, and is detailed in FIGS. 2B and 3 to which reference is now made.

Figure 2B:
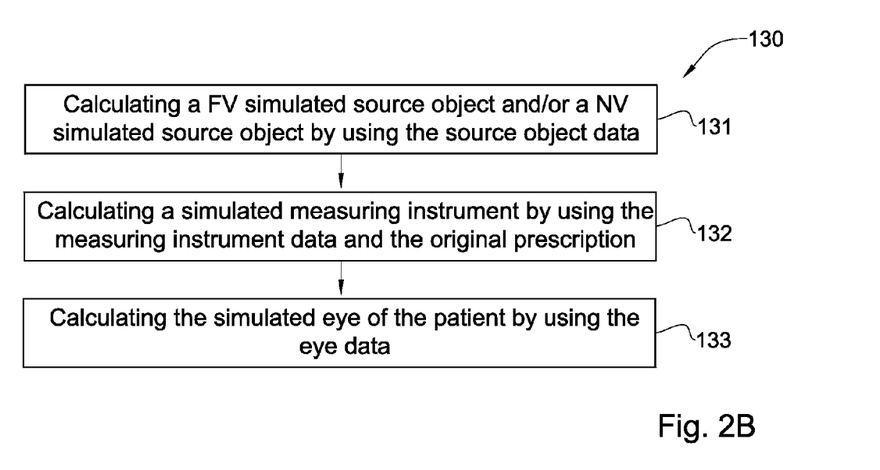
FIG. 2B generally illustrates sub-steps of step of calculating a simulated optical system that simulates the real optical system.

According to FIG. 2B, there are three steps according to which the simulated optical system 300 of step 130 is generated, as follows:

In step 131 of step 130, the position of a FV simulated source object 210 and/or a NV simulated source object 220 is calculated using the source object data. The FV simulates source object 210 simulates the FV real source object (e.g., the testing board 30), and the NV simulated source object 220 simulates the NV real source object (e.g., the book 70).

In step 132 of step 130, a simulated measuring instrument 230 is calculated using the measuring instrument data and the original prescription. The simulated measuring instrument 230 simulates the real measuring instrument (e.g., the trial frame 20 for FV, the trial frame 80 for NV).

In step 133 of step 130, a simulated eye 240 (or two simulated eyes which are not shown) of the patient is calculated using the eye data. The simulated eye 240 of the patient simulates the real eye of patient (e.g., eyes 12, eyes 62).

The FV simulated source object 210, the NV simulated source object 220, the simulated measuring instrument 230, and the simulated eye 240 of the simulated optical system 300 are geometrical and physical representation (i.e., position, orientation, dimensions and optical characteristics) of the real optical system's components in which the eye vision measurement procedure has been performed. In order to represent the real optical system by means of the simulated optical system, the OSB algorithm, being represented by the step 130, geometrically and physically characterizes each one of its components by using the supplementary input data and data of the original prescription. Each one the simulated optical system's components has its own corresponding parameters, selected from the supplementary input data, according to which it is simulated, as detailed below.

In order to represent the FV simulated source object 210 (when a FV measurement was performed), its simulated geometrical position is calculated in step 131 by using one or more of the following parameters of the simulated object data: FV object distance from patient, FV usage of mirrors, FV height of FV object with respect to the floor, FV vertical height of patient's eye from the floor, FV vertical height difference between the FV object and the patient's eye, and FV compensation of lens sphere power measurement. For example, by knowing the value of the FV object distance from patient, the distance $D_1$ can be calculated in order to position the FV simulated source object 210 in the simulated optical system 300 with respect to the simulated eye 240.

In order to represent the NV simulated source object 220 (when a NV measurement was performed), its geometrical position is calculated in step 131 by using one or more of the following parameters of the simulated object data: NV object distance measurement, NV vertical observation angle of patient, phoropter lens diameter and trial frame lens diameter. For example, by knowing the value of the NV object distance measurement, the distance $D_2$ can be calculated in order to position the NV simulated source object 220 in the simulated optical system 300 with respect to the simulated eye 240.

In order to represent the simulated measuring instrument 230, its simulated geometrical position, geometrical orientation, and optical and geometrical characteristics are calculated in step 132 by using one or more of the parameters of the measurement instrument data.

In order to represent the geometrical position of the simulated measuring instrument 230 for simulating the geometrical position of the real measuring instrument, one or more of the following parameters of the measurement instrument data is used: FV BVD between the measuring instrument in NV vision measurement and the eye of the patient, FV taking into consideration of the BVD, NV BVD between the measuring instrument in NV vision measurement and the eye of the patient, NV taking into consideration of the BVD, FV type of measuring instrument, NV type of measuring instrument, phoropter parameters, FV number of lenses and their position in trial frame slots, and NV number of lenses and their position in trial frame slots. For example, if a phoropter was used in the eye vision measurement procedure, the phoropter parameters can be used for determining the geometrical position of the lenses in the simulated measurement system, according to the phoropter's specification that includes the phoropter's brand and model. If a trail frame was used in the eye vision measurement procedure, the FV number of lenses and their position in trial frame slots (for FV) or NV number of lenses and their position in trial frame slots (for NV) can be used for determining the geometrical position of the lenses in the simulated measurement system, according to the trial frame's specification.

In order to represent the geometrical orientation of the simulated measuring instrument 230 for simulating the geometrical orientation of the real measuring instrument, one or more of the following parameters of the measurement instrument data is used: FV vertical tilt of the measuring instrument, NV vertical tilt of the measuring instrument, FV horizontal tilt of the measuring instrument, NV horizontal tilt of the measuring instrument, FV vertical observation angle of patient, NV vertical observation angle of patient, FV horizontal observation angle of patient, and NV horizontal observation angle of patient.

In order to represent the optical and geometrical characteristics of the simulated measuring instrument 230 for simulating the optical and geometrical characteristics of the real measuring instrument, one or more of the following parameters of the measurement instrument data is used: phoropter parameters, and trial frame parameters. As mentioned above, these parameters include data related to the specification the phoropter and the trial frame, which can be used for simulating the optical and geometrical characteristics of the real measuring instrument.

In order to represent the simulated eye 240, its pupil's simulated geometrical dimensions, geometrical position and orientation, and dimensions of a reference refraction surface 245 are calculated in step 133 using one or more of the parameters of the eye data.

In order to represent the eye 240 pupil's geometrical dimensions for simulating the geometrical dimensions of the pupil of the real eye of the patient, one or more of the following parameters of the eye data is used: FV strength of illumination during the eye vision measurement, NV strength of illumination during the eye vision measurement, FV pupil diameter, and NV pupil diameter.

In order to represent geometrical position and orientation of the simulated eye 240 for simulating the geometrical position and orientation of the real eye of the patient, one or more of the following parameters of the eye data is used: FV horizontal tilt of the measuring instrument, NV horizontal tilt of the measuring instrument, FV horizontal observation angle of patient, and NV horizontal observation angle of patient.

The reference refraction surface can be any surface between the back surface of the measurement instrument and the patient's eye, but it is usually the back vertex sphere. In order to represent dimensions of reference refraction surface of the simulated eye 240 for simulating the dimensions of reference refraction surface of the real eye of the patient, the FV BVD between the measuring instrument in FV vision measurement and the eye of the patient or the NV BVD between the measuring instrument in NV vision measurement and the eye of the patient can be used for the calculation. For example, as shown in FIG. 3, a reference refraction surface 245 is similar to the back vertex sphere which is defined as a normal to patient's line of sight at a distance of BVD+el/2 from the center of the eye, where el is the eye-length and its default value can be approximately 28 mm, and BVD is the Back Vertex Distance which can be calculated from the FV BVD between the measuring instrument in FV vision measurement and the eye of the patient or from the NV BVD between the measuring instrument in NV vision measurement and the eye of the patient.

The step 130 can be expressed by the following equation:

$$OS_{OPT} = OSB(Rx^{OPT}, SID^{OPT})$$

when $Rx^{OPT}$ is the original prescription, $SID^{OPT}$ is the supplementary input data, OSB( ) is the optical system builder function (algorithm), and $OS^{OPT}$ is the simulated optical system.

Figure 4A:
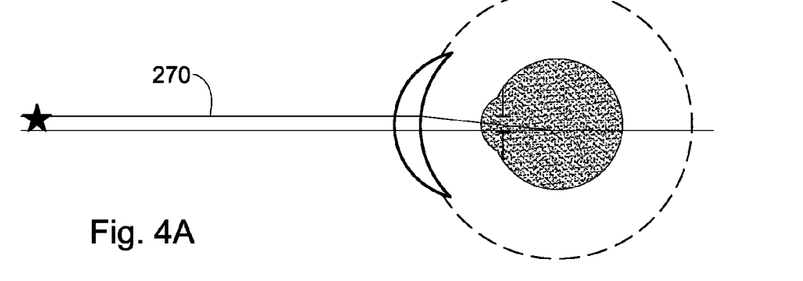
FIGS. 4A-B schematically illustrates the process of ray tracing which can be performed by the system and method of the presently disclosed subject matter.
Figure 4B:
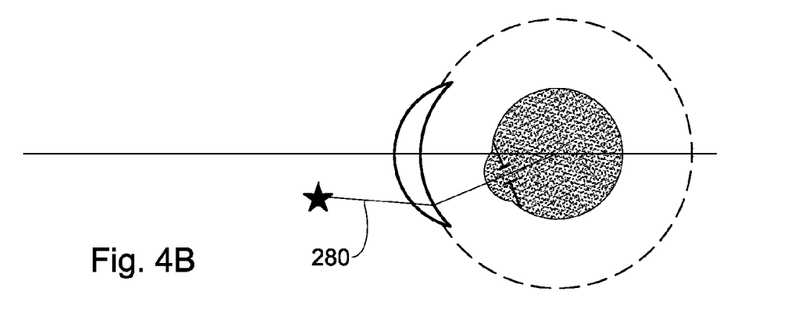

In step 140 of the method 200 of FIG. 2A, an adjusted prescription on the reference refraction surface 245 is calculated by using the original prescription and the simulated optical system as received from step 130. The adjusted prescription reflects the effect of the supplementary input data on the eye vision measurement procedure. The calculation of the adjusted prescription is performed by simulating wave fronts propagation from the FV or NV simulated source object (according to the FV or NV measurement procedure) through the simulated measurement instrument towards the simulated eye. The process of ray tracing is illustrated in FIGS. 4A and 4B for FV and NV, respectively, and is represented by lines 270 and 280, correspondingly.

The step 140 is well known procedure in the art. It is designated herein by an optical operator O( ), such as the optical operator of Stavroudis which is disclosed in the scientific paper: O. N. Stavroudis, "*The Optics of Rays, Wavefronts and Caustics*" (Academic Press, Optics & Laser Technology, vol. 5, issue 3, p. 143, 1972), the content of which is incorporated by reference. This paper discloses a method, based on eikonal functions, for calculating the localized refracted wavefronts beyond the optical element. The eikonal method, according to which the optical operator O( ) is defined, involves precomputing eikonal functions and geometrical quantities related to the known and initial surfaces. It provides an efficient explicit computation of the localized refracted wavefronts, and provides an explicit computation of the coefficients which in the final term characterize the adjusted prescription on the reference refraction surface 245.

The step 140 can be expressed by the following equation:

$$Rx^{ADJ}=O(Rx^{OPT},OS_{OPT}).$$

where $Rx^{OPT}$ is the original prescription, $OS_{OPT}$ is the simulated optical system, O( ) is the optical operator defined above, and $Rx^{ADJ}$ is the adjusted prescription.

Figure 2C:
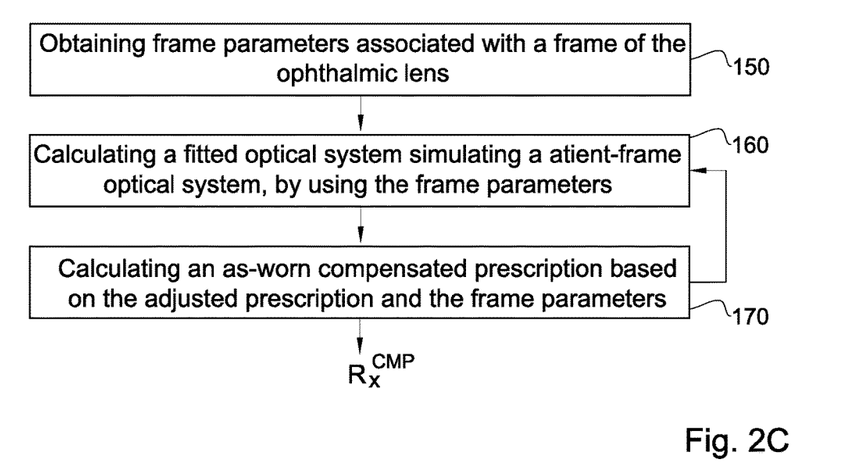
FIG. 2C generally illustrates the steps of a method according to the presently disclosed subject matter, which can be performed for calculating an as-worn compensated prescription according to the chosen frame of the ophthalmic lenses.

Reference is now made to FIG. 2C that illustrates a method 201 which uses the adjusted prescription for calculating an as-worn compensated prescription.

In step 150 of the method 201, frame parameters associated with a frame of the ophthalmic lens are obtained. This frame is the one the patient has chosen, in which the ophthalmic lenses will be installed. The frame parameters can be, for example, frame pantoscopic tilt, frame panoramic tilt, frame BVD, frame width, frame height, bridge width, and distance between lenses. All these are parameters known in the art which geometrically characterize a frame for ophthalmic lenses.

The steps 150, 160 and 170 of the method 201 are performed iteratively to calculate the as-worn compensated prescription.

The steps 160 and 170 can be expressed by the following equations:

$$OS_{FIT}=OSB(Rx^{CMP},SID^{FIT}) \qquad (I)$$

$$Rx^{ADJ}=O(Rx^{CMP},OS_{FIT}) \qquad (II)$$

where $Rx^{CMP}$ is the as-worn compensated prescription, $SID^{FIT}$ are the frame parameters of the chosen frame, $OS_{FIT}$ is the fitted optical system as will be perceived by the patient with the lenses in the chosen frame, $Rx^{ADJ}$ is the adjusted prescription, O( ) is the optical operator defined above, and OSB( ) is the optical system builder operator which is used at this time for simulating an optical system according to the chosen frame and the patient's eyes.

Eq. (I) and (II) are solved iteratively for the as-worn compensated prescription $Rx^{CMP}$. In order to solve these equations, an initial guess is used for $Rx^{CMP}$ (e.g. $Rx^{ADJ}$).

Then the algorithm solves the equation $O(Rx^{CMP}, OSB(Rx^{CMP}, SID^{FIT}))=Rx^{ADJ}$ by using optimization techniques known in the art.

The calculation of the as-worn compensated prescriptions $Rx^{CMP}$ can be subsequently provided to an ophthalmic lenses manufacturing machine to produce the ophthalmic lenses. The computation steps of the methods 200 and 201 can be performed by an electronic processing system configured to execute these steps. The electronic processing system can include a computer having electronic processor with a display device and an input device. The electronic processor of the computer is configured to execute one or more steps of the method according to the presently disclosed subject matter. For example, the computer can perform step 130 (including 131, 132 and 133) and step 140 of method 200 and steps 160 and 170 of the method 201.

According to another example, the invention features a computer-readable medium having computer executable instructions for performing the method and/or for storing the supplementary input data and the original prescription.

Examples

Table 1 includes examples of default values of supplementary input data parameters. When the real values of these default values are different in a specific eye vision measurement, they are usually not taken into consideration when an original prescription is provided.

TABLE 1

Default values of exemplary supplementary input data

| Parameter (from the supplementary input data) | Default value of the parameter |
|---|---|
| 1 FV object distance from patient | 6 meter |
| 2 FV vertical observation angle of patient | 0° |
| 3 FV horizontal observation angle of patient | 0° |
| 4 FV number of lenses and their position in trial frame slots | 1 lens in slot No. 3 |
| 5 FV vertical tilt of the measuring instrument | 0° |
| 6 FV horizontal tilt of the measuring instrument | 0° |
| 7 FV back vertex distance | 18 mm |
| 8 NV object distance measurement | 0.4 meter |
| 9 NV vertical observation angle of patient | −12° |
| 10 NV horizontal observation angle of patient | 0° |
| 11 NV number of lenses and their position in trial frame slots | 1 lens in slot No. 3 |
| 12 NV vertical tilt of the measuring instrument | 0° |
| 13 NV horizontal tilt of the measuring instrument | 0° |
| 14 NV back vertex distance | 18 mm |

Table 2 presents the default value of the trial frame lenses which can be stored in the parameter of trial frame lens diameter of the supplementary input data.

TABLE 2

Value of the parameter trial frame lens diameter

| Sphere power [D] | Central Thickness [mm] |
|---|---|
| −6 | 3.1 |
| −4 | 2.42 |
| −3 | 2.6 |
| −2 | 2.75 |
| −1 | 2.8 |
| 1 | 2.8 |
| 2 | 3.03 |
| 3 | 2.8 |
| 4 | 3.03 |

TABLE 2-continued

Value of the parameter trial frame lens diameter

| Sphere power [D] | Central Thickness [mm] |
|---|---|
| 6 | 3.1 |
| 7 | 3.2 |

Table 3 presents values of parameters of an original prescription being prescriber to a patient in 3 different hypothetical test cases. These test cases present prescriptions for NV and FV vision correction. The parameters of the original prescription in this table are: FV sphere power, FV cylinder power, NV sphere power, NV Cylinder Power, NV Addition Power. The values of these parameters are adjusted by the system and method of the presently disclosed subject matter.

TABLE 3 values of parameters of an original prescription

| | FV | | NV | | |
|---|---|---|---|---|---|
| Test Case | FV sphere power [D] | FV cylinder power [D] | NV sphere power [D] | NV Cylinder Power [D] | NV Addition Power [D] |
| 1 | −1 | 0 | +1 | 0 | +2 |
| 2 | −6 | 0 | −3 | 0 | +3 |
| 3 | +4 | 0 | +7 | 0 | +3 |

Table 4 presents 13 different scenarios of changes in the parameters of Table 1, and its influence on the parameters of test case 1 of the original prescription in Table 3.

TABLE 4 adjusted prescription in different scenarios for test case 1.

| | Far Vision | | Near Vision | | |
|---|---|---|---|---|---|
| Changed Parameters | Adjusted FV sphere power [D] | Adjusted FV cylinder power [D] | Adjusted NV sphere power [D] | Adjusted NV Cylinder Power [D] | Adjusted NV Addition Power [D] |
| $D_{FAR}$ = 4 m (with distance compensation) | −0.994 | 0 | 1.009 | −0.035 | 2.003 |
| $D_{FAR}$ = 4 m (without distance compensation) | −1.077 | 0 | 1.009 | −0.035 | 2.086 |
| $D_{NEAR}$ = 0.3 m (with distance compensation) | −0.995 | 0 | 0.996 | −0.031 | 1.991 |
| $D_{NEAR}$ = 0.3 m (without distance compensation) | −0.995 | 0 | 0.163 | −0.031 | 1.158 |
| Far vision, $\alpha_{ver}$ = 5° | −1.001 | −0.007 | 1.009 | −0.035 | 2.01 |
| Near vision, $\alpha_{ver}$ = 0° | −0.995 | 0 | 0.98 | 0 | 1.975 |
| $\theta_{panto}$ = 9° | −1.015 | −0.026 | 0.986 | −0.007 | 2.001 |
| $\theta_{panor}$ = 6° | −1.002 | −0.015 | 1.018 | −0.047 | 2.02 |
| $P_{slot}$ = 1 | −1.008 | 0 | 1.053 | −0.04 | 2.061 |
| $P_{slot}$ = 5 | −0.987 | 0 | 0.984 | −0.032 | 1.971 |
| Near vision: $n_{lens}$ = 2, −1 [D] in $P_{slot}$ = 3 + 2 [D] in $P_{slot}$ = 1 | −0.995 | 0 | 1.103 | −0.035 | 2.098 |
| Near vision: $n_{lens}$ = 2, −1 [D] in $P_{slot}$ = 3 + 2 [D] in $P_{slot}$ = 5 | −0.995 | 0 | 0.972 | −0.032 | 1.967 |
| Combined case: $P_{slot}$ = 1, $\theta_{panto}$ = 9° Far vision, $\alpha_{ver}$ = 5° Near vision, $\alpha_{ver}$ = −20° | −1.061 | −0.063 | 1.05 | −0.021 | 2.111 |

Table 5 presents 13 different scenarios of changes in the parameters of Table 1, and its influence on the parameters of test case 2 of the original prescription in Table 3.

TABLE 5 adjusted prescription in different scenarios for test case 2.

| | Far Vision | | Near Vision | | |
|---|---|---|---|---|---|
| Changed Parameters | Adjusted FV sphere power [D] | Adjusted FV cylinder power [D] | Adjusted NV sphere power [D] | Adjusted NV Cylinder Power [D] | Adjusted NV Addition Power [D] |
| $D_{FAR}$ = 4 m (with distance compensation) | −5.868 | 0 | −3 | −0.091 | 2.868 |

TABLE 5-continued adjusted prescription in different scenarios for test case 2.

| Changed Parameters | Far Vision | | Near Vision | | |
|---|---|---|---|---|---|
| | Adjusted FV sphere power [D] | Adjusted FV cylinder power [D] | Adjusted NV sphere power [D] | Adjusted NV Cylinder Power [D] | Adjusted NV Addition Power [D] |
| $D_{FAR}$ = 4 m (without distance compensation) | −5.951 | 0 | −3 | −0.091 | 2.951 |
| $D_{NEAR}$ = 0.3 m (with distance compensation) | −5.871 | 0 | −2.978 | −0.079 | 2.893 |
| $D_{NEAR}$ = 0.3 m (without distance compensation) | −5.871 | 0 | −3.811 | −0.079 | 2.06 |
| Far vision, $\alpha_{ver}$ = 5° | −5.906 | −0.041 | −3 | −0.091 | 2.906 |
| Near vision, $\alpha_{ver}$ = 0° | −5.871 | 0 | −2.922 | 0 | 2.949 |
| $\theta_{panto}$ = 9° | −5.991 | −0.148 | −2.923 | −0.02 | 3.068 |
| $\theta_{panor}$ = 6° | −5.915 | −0.083 | −3.027 | −0.144 | 2.888 |
| $P_{slot}$ = 1 | −6.259 | 0 | −3.265 | −0.117 | 2.994 |
| $P_{slot}$ = 5 | −5.66 | 0 | −2.857 | −0.078 | 2.803 |
| Near vision: $n_{lens}$ = 2, −1 [D] in $P_{slot}$ = 3 + 2 [D] in $P_{slot}$ = 1 | −5.871 | 0 | −2.654 | −0.074 | 3.217 |
| Near vision: $n_{lens}$ = 2, −1 [D] in $P_{slot}$ = 3 + 2 [D] in $P_{slot}$ = 5 | −5.871 | 0 | −3.057 | −0.113 | 2.814 |
| Combined case: $P_{slot}$ = 1, $\theta_{panto}$ = 9° Far vision, $\alpha_{ver}$ = 5° Near vision $\alpha_{ver}$ = −20° | −6.591 | −0.39 | −3.236 | −0.104 | 3.355 |

Table 6 presents 13 different scenarios of changes in the parameters of Table 1, and its influence on the parameters of test case 3 of the original prescription in Table 3.

TABLE 6 adjusted prescription in different scenarios for test case 3.

| Changed Parameters | Far Vision | | Near Vision | | |
|---|---|---|---|---|---|
| | Adjusted FV sphere power [D] | Adjusted FV cylinder power [D] | Adjusted NV sphere power [D] | Adjusted NV Cylinder Power [D] | Adjusted NV Addition Power [D] |
| $D_{FAR}$ = 4 m (with distance compensation) | 4.05 | 0 | 7.314 | −0.329 | 3.264 |
| $D_{FAR}$ = 4 m (without distance compensation) | 3.967 | 0 | 7.314 | −0.329 | 3.347 |
| $D_{NEAR}$ = 0.3 m (with distance compensation) | 4.052 | 0 | 7.247 | −0.302 | 3.195 |
| $D_{NEAR}$ = 0.3 m (without distance compensation) | 4.052 | 0 | 6.414 | −0.302 | 2.362 |
| Far vision, $\alpha_{ver}$ = 5° | 4.08 | −0.034 | 7.314 | −0.329 | 3.234 |
| Near vision, $\alpha_{ver}$ = 0° | 4.052 | 0 | 7.043 | 0 | 2.991 |
| $\theta_{panto}$ = 9° | 4.138 | −0.102 | 7.099 | −0.009 | 2.961 |
| $\theta_{panor}$ = 6° | 4.096 | −0.032 | 7.383 | −0.403 | 3.287 |
| $P_{slot}$ = 1 | 3.907 | 0 | 7.143 | −0.291 | 3.236 |
| $P_{slot}$ = 5 | 4.145 | 0 | 7.434 | −0.359 | 3.289 |
| Near vision: $n_{lens}$ = 2, −1 [D] in $P_{slot}$ = 3 + 2 [D] in $P_{slot}$ = 1 | 4.052 | 0 | 7.095 | −0.284 | 3.043 |

TABLE 6-continued adjusted prescription in different scenarios for test case 3.

| | Far Vision | | Near Vision | | |
|---|---|---|---|---|---|
| Changed Parameters | Adjusted FV sphere power [D] | Adjusted FV cylinder power [D] | Adjusted NV sphere power [D] | Adjusted NV Cylinder Power [D] | Adjusted NV Addition Power [D] |
| Near vision: $n_{lens} = 2$, $-1$ [D] in $P_{slot} = 3 + 2$ [D] in $P_{slot} = 5$ | 4.052 | 0 | 7.259 | −0.306 | 3.207 |
| Combined case: $P_{slot} = 1$, $\theta_{panto} = 9°$ Far vision, $a_{ver} = 5°$ Near vision, $\alpha_{ver} = -20°$ | 4.103 | −0.252 | 7.132 | −0.205 | 3.029 |

The invention claimed is:

1. A method for calculating an adjusted prescription for an eye of a patient using a simulated optical system run on a computing system, for use in manufacturing of an ophthalmic lens for correcting the vision of a patient, said method comprising:
   (a) at the computing system, receiving input data including an original prescription based on an eye vision measurement performed via a real optical system;
   (b) at the computing system, receiving supplementary input data associated with an eye vision measurement in which said original prescription was obtained, wherein said supplementary input data includes at least one of measuring instrument data from said eye vision measurement in which said original prescription was obtained, an eye data, or source object data from said eye vision measurement in which said original prescription was obtained;
   (c) with said simulated optical system run on the computing system, simulating said real optical system in which said eye vision measurement was performed; and
   (d) with the computing system and at least said simulation of said real optical system generated with said simulated optical system, said original prescription, and said supplementary input data, calculating an said adjusted prescription to compensate for an effect of said supplementary input data on said eye vision measurement;
   wherein said measuring instrument data includes one of a tilt of a measuring instrument, an observation angle of the patient, a geometry of the lens used in the measuring instrument, a refraction index of the lens used in the measuring instrument, a center thickness of the lens used in the measuring instrument, an edge thickness of the lens in the measuring instrument, or a diameter of the lens used in the measuring instrument; and
   wherein the eye data includes one of a strength of illumination during the eye measurement or a pupil diameter.

2. The method according to claim 1, wherein said measuring instrument data comprises at least one of: FV vertical tilt of the measuring instrument, NV vertical tilt of the measuring instrument, FV horizontal tilt of the measuring instrument, or NV horizontal tilt of the measuring instrument.

3. The method according to claim 1, wherein said measuring instrument data is associated with an observation angle of said patient.

4. The method according to claim 1, wherein said measuring instrument data comprises at least one of: FV vertical observation angle of patient, NV vertical observation angle of patient, FV horizontal observation angle of patient, or NV horizontal observation angle of patient.

5. An ophthalmic lens manufactured based on said adjusted prescription according to claim 1.

6. The method according to claim 1, wherein said measuring instrument data is associated with a tilt of a measuring instrument with which said original prescription was obtained.

7. The method according to claim 1, wherein said source object data includes at least one of FV object distance from said patient, FV usage of mirrors, FV height of FV object with respect to the floor, FV vertical height of said patient's eye from said floor, FV vertical height difference between said FV object and said patient's eye, and FV compensation of lens sphere power measurement, NV object distance measurement, NV vertical observation angle of patient, phoropter lens diameter, or trial frame lens diameter.

8. The method according to claim 1, wherein said source object data includes at least one of FV strength of illumination during said eye vision measurement, NV strength of illumination during said eye vision measurement, FV horizontal tilt of a measuring instrument used in said eye vision measurement, NV horizontal tilt of said measuring instrument used in said eye vision measurement, NV object distance measurement, FV horizontal observation angle of patient, or NV horizontal observation angle of said patient.

* * * * *